(12) United States Patent
Pallem et al.

(10) Patent No.: US 8,633,329 B2
(45) Date of Patent: Jan. 21, 2014

(54) TITANIUM-CONTAINING PRECURSORS FOR VAPOR DEPOSITION

(71) Applicant: American Air Liquide, Inc., Fremont, CA (US)

(72) Inventors: Venkateswara R. Pallem, Bear, DE (US); Christian Dussarrat, Tokyo (JP)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 13/772,737

(22) Filed: Feb. 21, 2013

(65) Prior Publication Data

US 2013/0164947 A1 Jun. 27, 2013

Related U.S. Application Data

(63) Continuation of application No. 12/981,872, filed on Dec. 30, 2010, now Pat. No. 8,404,878.

(60) Provisional application No. 61/321,763, filed on Apr. 7, 2010.

(51) Int. Cl.
*C23C 16/30* (2006.01)
*C23C 16/22* (2006.01)
*C23C 16/16* (2006.01)
*H01L 21/205* (2006.01)

(52) U.S. Cl.
USPC ............................. 556/56; 556/54; 427/248.1

(58) Field of Classification Search
None
See application file for complete search history.

(56) References Cited

U.S. PATENT DOCUMENTS

| 6,821,921 B2 | 11/2004 | Theopold et al. |
| 7,491,654 B2 | 2/2009 | Song et al. |
| 2005/0277223 A1 | 12/2005 | Lee et al. |

FOREIGN PATENT DOCUMENTS

| JP | 2006 45083 | 2/2006 |
| KR | 10 0584200 | 8/2005 |
| KR | 10 0640654 | 11/2006 |
| WO | WO 2007 012052 | 1/2007 |

OTHER PUBLICATIONS

Alluri, P. et al., "ECR-MOCVD of the Ba—Sr—Ti—O system below 400° C. * Part I: Processing," Integrated Ferroelectrics, 1998, vol. 21, pp. 305-318.
Chen, X-Q et al., "Reaction of titanium tetrabutoxide with acetic anhydride and structure analysis of the titanyl organic compounds products," Acta Chimica Sinica, 61(10), pp. 1592-1596, year 2003.
Cotton, S.A., "Titanium, zirconium and hafnium," Annu. Rep. Prog. Che., Sect. A, Aug. 9, 2001, vol. 97, pp. 133-142.
Durand, H.-A. et al., "Excimer laser sputtering deposition of $TiO_2$ optical coating for solar cells," Applied Surface Science 86 (1995) pp. 122-127.
Hwang, C.S. et al., "Deposition and electrical characterization of very thin $SrTiO_3$ films for ultra large scale integrated dynamic random access memory application," Japan Journal of Applied Physics, vol. 34 (1995) p. 5178-5183.
Inoue, T. et al., "Photoelectrocatalytic reduction of carbon dioxide in aqueous suspensions of semiconductor powders," Nature, vol. 277, Feb. 22, 1979, pp. 637-638.
Katamreddy, R. et al., "Ti source precursors for atomic layer deposition of $TiO_2$, STO and BST," 2008 ECS conference.
Keshmiri, M. et al., "Apatite formation on $TiO_2$ anatase microspheres," Journal of Non-Crystalline Solids 324 (2003) pp. 289-294.
Kim, H. et al., "Laser processing of nanocrystalline $TiO_2$ films for dye-sensitized solar cells," Applied Physics Letters, vol. 85, No. 3, Jul. 19, 2004, pp. 464-466.
Scott, J.F. et al., "Ferroelectric memories," Science, vol. 246, Dec. 15, 1989, pp. 1400-1405.
Wang, C.-W. et al., "Gamma-ray-irradiation effects on the leakage current and reliability of sputtered $TiO_2$ gate oxide in metal-oxide-semiconductor capacitors," Journal of Applied Physics, vol. 91, No. 11, Jun. 1, 2002, pp. 9198-9203.
Zhang, Y. et al., "Unexpected carbon-oxygen bond cleavage of THF promoted by guanidinate titanium complex/lithium diisopropylamide: Synthesis and crystal structure," Chinese Science Bulletin (2005), 50(24), pp. 2817-2820.
International Search Report and Written Opinion for corresponding PCT/US2011/031346, Oct. 20, 2011.

*Primary Examiner* — Yevegeny Valenrod
(74) *Attorney, Agent, or Firm* — Patricia E. McQueeney

(57) ABSTRACT

Disclosed are titanium-containing precursors and methods of synthesizing the same. The compounds may be used to deposit titanium, titanium oxide, strontium-titanium oxide, and barium strontium titanate containing layers using vapor deposition methods such as chemical vapor deposition or atomic layer deposition.

16 Claims, 3 Drawing Sheets

TITANIUM-CONTAINING PRECURSORS FOR VAPOR DEPOSITION

CROSS-REFERENCE TO RELATED APPLICATIONS

This application is a continuation of U.S. patent application Ser. No. 12/981,872 filed Dec. 30, 2010, which claims the benefit under 35 U.S.C. §119(e) to provisional application No. 61/321,763, filed Apr. 7, 2010, the entire contents of each being incorporated herein by reference.

TECHNICAL FIELD

Disclosed are titanium-containing precursors, methods of synthesizing the same, and methods of using the same to deposit titanium-containing layers using vapor deposition processes.

BACKGROUND

One of the serious challenges the semiconductor industry faces is developing new gate dielectric materials for DRAM and capacitors. For decades, silicon dioxide ($SiO_2$) was a reliable dielectric, but as transistors have continued to shrink and the technology has moved from "Full Si" transistors to "Metal Gate/High-k" transistors, the reliability of the $SiO_2$-based gate dielectric is reaching its physical limits. The need for new high dielectric constant materials and processes is increasing and becoming more and more critical as the size for current technology shrinks.

Standard dielectric materials like $TiO_2$ or new dielectric materials containing alkaline earth metals called strontium titanates, such as $SrTiO_3$ or $Sr_2TiO_4$, or barium strontium titanates provide a significant advantage in capacitance compared to conventional dielectric materials. The new dielectric materials are also attractive candidates for several thin film applications, such as high dielectric constant materials for electronic devices, anti-reflection optical coatings, biocompatible coatings, photocatalysis, and solar cells. (H. A. Durand et al., Appl. Surf. Sci. 86, 122 (1995); C.-W. Wang et al., J. Appl. Phys. 91, 9198 (2002); M. Keshmiri et al., J. Non-Cryst. Solids 324, 289 (2003); T. Inoue et al., Nature (London) 277,637 (1979); H. Kim et al., Appl. Phys. Lett. 85, 64 (2004)).

In addition, $TiO_2$ is also a constituent of several important multi-metal oxide systems, such as strontium titanates (STOs), barium strontium titanates (BSTs), and lead zirconium titanates (PZTs), for dielectric and ferroelectric applications. (P. Alluri et al., Integr. Ferroelectr., 21, 305 (1998); J. F. Scott et al., Science 246, 1400 (1989)).

Nevertheless, deposition of Ti containing layers is difficult and new materials and processes are needed. For instance, atomic layer deposition, ALD, has been identified as an important thin film growth technique for microelectronics manufacturing, relying on sequential and saturating surface reactions of alternatively applied precursors, separated by inert gas purging. Frequently, an oxygen source such as ozone or water is used in this deposition method. The surface-controlled nature of ALD enables the growth of thin films of high conformality and uniformity with an accurate thickness control.

In STO ALD deposition, available Sr precursors show excellent reactivity with $O_3$ and acceptable reactivity with water. However, the use of ozone as an oxidant may have undesired results with the underlying layer, such as TiN or strontium ruthenium oxide (SRO), when the STO film is deposited at high temperature. It may either oxidize the TiN layer or partially etch Ru from SRO layer.

Although atomic layer deposition (ALD) of Ti compounds has been disclosed, these metal precursors have poor reactivity, especially with moisture, and low stability often requiring low substrate temperatures and strong oxidizers to grow a film, which is often contaminated with carbon or nitrogen.

Air Liquide showed that most of the standard homoleptic Ti molecules have limited ALD process temperature window or no deposition (R. Katamreddy, V. Omarjee, B. Feist, C. Dussarrat, ECS conference 2008). For example, in a water ALD process, the Ti molecules titanium tetrakis(isopropoxide) (TTIP), tetrakis(dimethylamino) titanium (TDMAT), tetrakis(diethylamino) titanium (TDEAT), and tetrakis(ethylmethylamino) titanium (TEMAT) had deposition rates below 0.6 Å/cycle and process windows that did not exceed 250° C. Id.

New Ti precursors having higher thermal stability at higher process temperatures are needed. High temperature processes are desired to generate high quality $TiO_2$ (doped or undoped) and STO films with very high dielectric constants (preferably with k≥50). It has been reported that an STO film with a dense and columnar polycrystalline microstructure and a small average grain size (30 nm) is required to obtain a low leakage current with a high k value (C. S. Hwang, S. O. Park, C. S. Kang, H. Cho, H. Kang, S. T. Ahn, and M. Y. Lee, Jpn. J. Appl. Phys., Part 1, 34, 5178 1995).

Zhang et al. disclose the unexpected synthesis of $Ti(Cy\text{-}NC(NiPr_2)\ N\text{-}Cy)_2(OnBu)_2$. Chinese Science Bulletin (2005), 50(24), 2817-2820. Chen et al. disclose the synthesis of $Ti(OnBu)_2(O2CMe)_2$. Huaxue Xuebao (2003), 61(10), 1592-1596. Uses for these compounds were not disclosed.

US Pat App Pub No 2005/277223 discloses ALD methods of forming metal oxides using metal-containing precursors having the formula $M(L1)_x(L2)_y$, wherein M is a metal, L1 and L2 may be halide, diketonate, alkoxide, amino, alkoxyamine, amidinate, or multidentate ligands. The exemplary precursors however are only $Hf(OtBu)_2(NEtMe)_2$, $Hf(OtBu)_2(NEt_2)_2$, $Hf(NEt_2)_2(DMAMP)_2$, $Hf(NEtMe)_2(DMAMP)_2$, $Ti(OtBu)_3Cl$, $Ti(OtBu)_3Me$, $Ti(OtBu)_2(NEt_2)_2$, $Ti(NEt_2)_2(DMAMP)_2$, $Ti(OtBu)_2(DMAMP)_2$, and $TiCl_2(DMAMP)_2$.

Therefore, a need remains for precursors suitable for titanium/$H_2O$ ALD processes compatible with Sr ALD process.

New chemical vapor deposition (CVD) processes are also required for Ti materials. Other sources and methods of incorporating Ti materials are being sought for new generations of integrated circuit devices. Novel precursors are needed.

SUMMARY

Disclosed are molecules having the following formula:

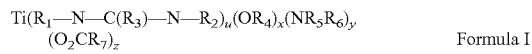

Formula I or

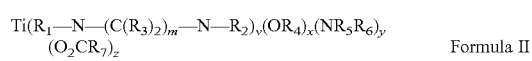

Formula II wherein:
$R_1, R_2, R_5, R_6$, and $R_7$ are independently selected from the group consisting of H and C1-C6 alkyl group;
$R_3$=H, C1-C6 alkyl group, or $NMe_2$;
$R_4$ is a C1-C6 alkyl group;
m=2-4;
u=0-2;
v=0-1;

x=1-3;
y=0-2;
z=0-1;
in Formula I, u+x+y+z=4;
in Formula II, 2v+x+y+z=4; and
u, v, or z≥1.

The disclosed molecules may further include one or more of the following aspects:

the molecule having Formula I, wherein u=1, x=3, y=0, and z=0;

the molecule being selected from the group consisting of Ti(iPr—N═C(Me)-N-iPr)$_1$(OiPr)$_3$, Ti(iPr—N═C(Me)-N-iPr)$_1$(OMe)$_3$, Ti(iPr—N═C(Me)-N-iPr)$_1$(OEt)$_3$, Ti(iPr—N═C(Me)-N-iPr)$_1$(OnPr)$_3$, Ti(iPr—N═C(Me)-N-iPr)$_1$(OsBu)$_3$, Ti(iPr—N═C(Me)-N-iPr)$_1$(OiBu)$_3$, Ti(iPr—N═C(Me)-N-iPr)$_1$(OtBu)$_3$, Ti(Et-N═C(Me)-N-Et)$_1$(OEt)$_3$, Ti(Et-N═C(Me)-N-Et)$_1$(OMe)$_3$, Ti(Et-N═C(Me)-N-Et)$_1$(OnPr)$_3$, Ti(Et-N═C(Me)-N-Et)$_1$(OsBu)$_3$, Ti(Et-N═C(Me)-N-Et)$_1$(OiBu)$_3$, Ti(Et-N═C(Me)-N-Et)$_1$(OtBu)$_3$, and Ti(iPr—N═C(NMe$_2$)—N-iPr)(OiPr)$_3$;

the molecule having Formula II, wherein v=1, x=2, y=0, and z=0;

The molecule being selected from the group consisting of Ti(iPr—N—(CH$_2$)$_2$—N-iPr)$_1$(OiPr)$_2$, Ti(iPr—N—(CH$_2$)$_2$—N-iPr)$_1$(OMe)$_2$, Ti(iPr—N—(CH$_2$)$_2$—N-iPr)$_1$(OEt)$_2$, Ti(iPr—N—(CH$_2$)$_2$—N-iPr)$_1$(OnPr)$_2$, Ti(iPr—N—(CH$_2$)$_2$—N-iPr)$_1$(OsBu)$_2$, Ti(iPr—N—(CH$_2$)$_2$—N-iPr)$_1$(OiBu)$_2$, Ti(iPr—N—(CH$_2$)$_2$—N-iPr)$_1$(OtBu)$_2$, Ti(Et-N—(CH$_2$)$_2$—N-Et)$_1$(OiPr)$_2$, Ti(Et-N—(CH$_2$)$_2$—N-Et)$_1$(OMe)$_2$, Ti(Et-N—(CH$_2$)$_2$—N-Et)$_1$(OEt)$_2$, Ti(Et-N—(CH$_2$)$_2$—N-Et)$_1$(OnPr)$_2$, Ti(Et-N—(CH$_2$)$_2$—N-Et)$_1$(OsBu)$_2$, Ti(Et-N—(CH$_2$)$_2$—N-Et)$_1$(OiBu)$_2$, Ti(Et-N—(CH$_2$)$_2$—N-Et)$_1$(OtBu)$_2$, Ti(iPr—N—(CH$_2$)$_3$—N-iPr)$_1$(OiPr)$_2$, Ti(iPr—N—(CH$_2$)$_3$—N-iPr)$_1$(OMe)$_2$, Ti(iPr—N—(CH$_2$)$_3$—N-iPr)$_1$(OEt)$_2$, Ti(iPr—N—(CH$_2$)$_3$—N-iPr)$_1$(OnPr)$_2$, Ti(iPr—N—(CH$_2$)$_3$—N-iPr)$_1$(OsBu)$_2$, Ti(iPr—N—(CH$_2$)$_3$—N-iPr)$_1$(OiBu)$_2$, Ti(iPr—N—(CH$_2$)$_3$—N-iPr)$_1$(OtBu)$_2$, Ti(Et-N—(CH$_2$)$_3$—N-Et)$_1$(OiPr)$_2$, Ti(Et-N—(CH$_2$)$_3$—N-Et)$_1$(OMe)$_2$, Ti(Et-N—(CH$_2$)$_3$—N-Et)$_1$(OEt)$_2$, Ti(Et-N—(CH$_2$)$_3$—N-Et)$_1$(OnPr)$_2$, Ti(Et-N—(CH$_2$)$_3$—N-Et)$_1$(OsBu)$_2$, Ti(Et-N—(CH$_2$)$_3$—N-Et)$_1$(OiBu)$_2$, and Ti(Et-N—(CH$_2$)$_3$—N-Et)$_1$(OtBu)$_2$;

the molecule having Formula I, wherein u=2, x=2, y=0, and z=0;

the molecule being selected from the group consisting of Ti(iPr—N═C(H)—N-iPr)$_2$(OiPr)$_2$, Ti(iPr—N═C(H)—N-iPr)$_2$(OMe)$_2$, Ti(iPr—N═C(H)—N-iPr)$_2$(OEt)$_2$, Ti(iPr—N═C(H)—N-iPr)$_2$(OnPr)$_2$, Ti(iPr—N═C(H)—N-iPr)$_2$(OsBu)$_2$, Ti(iPr—N═C(H)—N-iPr)$_2$(OiBu)$_2$, Ti(iPr—N═C(H)—N-iPr)$_2$(OtBu)$_2$, Ti(Et-N═C(H)—N-Et)$_2$(OiPr)$_2$, Ti(Et-N═C(H)—N-Et)$_2$(OMe)$_2$, Ti(Et-N═C(H)—N-Et)$_2$(OEt)$_2$, Ti(Et-N═C(H)—N-Et)$_2$(OnPr)$_2$, Ti(Et-N═C(H)—N-Et)$_2$(OsBu)$_2$, Ti(Et-N═C(H)—N-Et)$_2$(OiBu)$_2$, Ti(Et-N═C(H)—N-Et)$_2$(OtBu)$_2$, Ti(iPr—N═C(Me)-N-iPr)$_2$(OiPr)$_2$, Ti(iPr—N═C(Me)-N-iPr)$_2$(OMe)$_2$, Ti(iPr—N═C(Me)-N-iPr)$_2$(OEt)$_2$, Ti(iPr—N═C(Me)-N-iPr)$_2$(OnPr)$_2$, Ti(iPr—N═C(Me)-N-iPr)$_2$(OsBu)$_2$, Ti(iPr—N═C(Me)-N-iPr)$_2$(OiBu)$_2$, Ti(iPr—N═C(Me)-N-iPr)$_2$(OtBu)$_2$, Ti(Et-N═C(Me)-N-Et)$_2$(OiPr)$_2$, Ti(Et-N═C(Me)-N-Et)$_2$(OMe)$_2$, Ti(Et-N═C(Me)-N-Et)$_2$(OEt)$_2$, Ti(Et-N═C(Me)-N-Et)$_2$(OnPr)$_2$, Ti(Et-N═C(Me)-N-Et)$_2$(OsBu)$_2$, Ti(Et-N═C(Me)-N-Et)$_2$(OiBu)$_2$, and Ti(Et-N═C(Me)-N-Et)$_2$(OtBu)$_2$;

the molecule having Formula I, wherein u=1, x=2, y=1, and z=0;

the molecule being selected from the group consisting of Ti(iPr—N═C(Me)-N-iPr)(OiPr)$_2$(NMe$_2$), Ti(iPr—N═C(Me)-N-iPr)(OiPr)$_2$(NEt$_2$), Ti(iPr—N═C(Me)-N-iPr)(OiPr)$_2$(NEtMe), Ti(Et-N═C(Me)-N-Et)(OiPr)$_2$(NMe$_2$), Ti(Et-N═C(Me)-N-Et)(OiPr)$_2$(NEt$_2$), Ti(Et-N═C(Me)-N-Et)(OiPr)$_2$(NEtMe), Ti(iPr—N═C(NMe$_2$)—N-iPr)(OiPr)$_2$(NMe$_2$), Ti(iPr—N═C(NMe$_2$)—N-iPr)(OiPr)$_2$(NEt$_2$), and Ti(iPr—N═C(NMe$_2$)—N-iPr)(OiPr)$_2$(NEtMe);

the molecule having Formula I, wherein u=1, x=2, y=0, and z=1;

the molecule being selected from the group consisting of Ti(iPr—N═C(Me)-N-iPr)(OiPr)$_2$(O$_2$CMe) and Ti(Et-N═C(Me)-N-Et)(OiPr)$_2$(O$_2$CMe);

the molecule having Formula II, wherein v=1, x=1, y=0, and z=1;

The molecule being selected from the group consisting of Ti(iPr—N—(CH$_2$)$_2$—N-iPr)(OiPr)(O$_2$CMe), Ti(iPr—N—(CH$_2$)$_2$—N-iPr)(OMe)(O$_2$CMe), Ti(iPr—N—(CH$_2$)$_2$—N-iPr)(OEt)(O$_2$CMe), Ti(iPr—N—(CH$_2$)$_2$—N-iPr)(OnPr)(O$_2$CMe), Ti(iPr—N—(CH$_2$)$_2$—N-iPr)(OsBu)(O$_2$CMe), Ti(iPr—N—(CH$_2$)$_2$—N-iPr)(OiBu)(O$_2$CMe), Ti(iPr—N—(CH$_2$)$_2$—N-iPr)(OtBu)(O$_2$CMe), Ti(Et-N—(CH$_2$)$_2$—N-Et)(OiPr)(O$_2$CMe), Ti(Et-N—(CH$_2$)$_2$—N-Et)(OMe)(O$_2$CMe), Ti(Et-N—(CH$_2$)$_2$—N-Et)(OEt)(O$_2$CMe), Ti(Et-N—(CH$_2$)$_2$—N-Et)(OnPr)(O$_2$CMe), Ti(Et-N—(CH$_2$)$_2$—N-Et)(OsBu)(O$_2$CMe), Ti(Et-N—(CH$_2$)$_2$—N-Et)(OiBu)(O$_2$CMe), and Ti(Et-N—(CH$_2$)$_2$—N-Et)(OtBu)(O$_2$CMe);

the molecule having either Formula I or Formula II, wherein u, v, y=0, x=2, and z=2;

the molecule being Ti(OiPr)$_2$(O$_2$CMe)$_2$;

the molecule having either Formula I or Formula II, wherein u, v, y=0, x=3, and z=1; and the molecule being Ti(OiPr)$_3$(O$_2$CMe).

Also disclosed are methods of forming a Ti-containing layer on a substrate. A reaction chamber is provided having at least one substrate disposed within it. The vapor of at least one of the molecules disclosed above is introduced into the reaction chamber. The vapor is contacted with the substrate to form a Ti-containing layer on at least one surface of the substrate using a vapor deposition process. The disclosed methods may further include one or more of the following aspects:

introducing into the reaction chamber a second vapor including at least one metal-containing precursor and contacting the second vapor with the substrate to form a metal-containing layer on at least one surface of the substrate using the vapor deposition process, wherein the metal-containing precursor is selected from the group consisting of M(L)$_2$ and M(L)$_2$.A, wherein:

M is Sr or Ba;

L is selected from substituted cyclopentadienyl ligand systems R$_1$R$_2$R$_3$R$_4$R$_5$Cp or beta-diketonate ligand systems —O—CR$_6$—CH—CR$_7$—O—;

each of R$_1$ to R$_5$ is independently selected from H or C1-C6 linear or branched alkyl chain;

each of R$_6$ and R$_7$ is independently selected from C1-C6 linear or branched alkyl chain; and A is a neutral oxygen containing molecules selected from the group consisting of tetrahydrofuran, dimethoxyethane, diglyme, triglyme, and tetraglyme; and the metal-containing precursor being selected from the group consisting of Sr(iPr$_3$Cp)$_2$, Sr(iPr$_3$Cp)$_2$.thf, Sr(iPr$_3$Cp)$_2$.dme, Sr(tBu$_3$Cp)$_2$, Sr(tBu$_3$Cp)$_2$.thf, Sr(tBu₃Cp)₂.dme, Sr(thmd)₂, Sr(thmd)₂.triglyme, Sr(thmd)₂.tetraglyme, Sr(Me₅Cp)₂, Sr(Me₄Cp)₂, Sr(Me₄EtCp)₂, Sr(Me₄nBuCp)₂, Ba(iPr₃Cp)₂, Ba(iPr₃Cp)₂.thf, Ba(iPr₃Cp)₂.dme, Ba(tBu₃Cp)₂, Ba(tBu₃Cp)₂.thf, Ba(tBu₃Cp)₂.dme, Ba(thmd)₂, Ba(thmd)₂.triglyme, Ba(thmd)₂.tetraglyme, Ba(Me₅Cp)₂, Ba(Me₄Cp)₂, Ba(Me₄EtCp)₂, and Ba(Me₄nBuCp)₂.

Also disclosed are methods of depositing a STO or BST film. An ALD reaction chamber is provided having at least one substrate disposed within it. At least one of the compounds disclosed above is pulsed into the reaction chamber. An oxygen source is pulsed into the reaction chamber. A metal-containing precursor is pulsed into the reaction chamber. The metal-containing precursor is selected from the group consisting of M(L)₂ and M(L)₂.A, wherein:

M is Sr or Ba;
L is selected from substituted cyclopentadenyl ligand systems R₁R₂R₃R₄R₅Cp or beta-diketonate ligand systems —O—CR₆—CH—CR₇—O—;
each of R₁ to R₅ is independently selected from H or C1-C6 linear or branched alkyl chain;
each of R₆ and R₇ is independently selected from C1-C6 linear or branched alkyl chain; and
A is a neutral oxygen containing molecules selected from the group consisting of tetrahydrofuran, dimethoxyethane, diglyme, triglyme, and tetraglyme.

A second oxygen source is pulsed into the reaction chamber. The stoichiometry of M:Ti ratio in the STO or BST film is controlled by varying the number of pulsing steps for the precursor and metal-containing precursor. The disclosed methods may further include one or more of the following aspects:

the metal-containing precursor being selected from the group consisting of Sr(iPr₃Cp)₂, Sr(iPr₃Cp)₂.thf, Sr(iPr₃Cp)₂.dme, Sr(tBu₃Cp)₂, Sr(tBu₃Cp)₂.thf, Sr(tBu₃Cp)₂.dme, Sr(thmd)₂, Sr(thmd)₂.triglyme, Sr(thmd)₂.tetraglyme, Sr(MesCp)₂, Sr(Me₄Cp)₂, Sr(Me₄EtCp)₂, Sr(Me₄nBuCp)₂, Ba(iPr₃Cp)₂, Ba(iPr₃Cp)₂.thf, Ba(iPr₃Cp)₂.dme, Ba(tBu₃Cp)₂, Ba(tBu₃Cp)₂.thf, Ba(tBu₃Cp)₂.dme, Ba(thmd)₂, Ba(thmd)₂.triglyme, Ba(thmd)₂.tetraglyme, Ba(Me₅Cp)₂, Ba(Me₄Cp)₂, Ba(Me₄EtCp)₂, and Ba(Me₄nBuCp)₂; and the oxygen source and the second oxygen source being water.

Notation and Nomenclature

Certain abbreviations, symbols, and terms are used throughout the following description and claims and include: the abbreviation "STO" refers to strontium titanates; the abbreviation "BST" refers to barium strontium titanates; the abbreviation "PZT" refers to lead zirconium titanates;
the abbreviation "R₁—NC(R₃)N—R₂" refers to the following chemical structure:

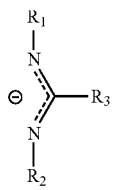

the abbreviation "R₁—N(C(R₃)₂)ₘ—N—R₂" refers to the following chemical structure:

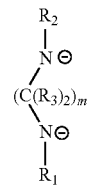

the abbreviation "O₂CR₇" refers to the following chemical structure:

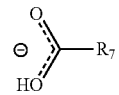

the abbreviation "Cy" refers to cyclohexyl; the abbreviation "Cp" refers to cyclopentadiene; the term "aliphatic group" refers to a C1-C6 linear or branched chain alkyl group; the term "alkyl group" refers to saturated functional groups containing exclusively carbon and hydrogen atoms and includes linear, branched, or cyclic alkyl groups. Examples of linear alkyl groups include without limitation, methyl groups, ethyl groups, n-propyl groups, n-butyl groups, etc. Examples of branched alkyls groups include without limitation, t-butyl. Examples of cyclic alkyl groups include without limitation, cyclopropyl groups, cyclobutyl groups, cyclopentyl groups, cyclohexyl groups, etc. The abbreviation "Me" refers to a methyl group; the abbreviation "Et" refers to an ethyl group; the abbreviation "Pr" refers to a propyl group; the abbreviation "iPr" refers to an isopropyl group; the abbreviation "iBu" refers to an isobutyl group; the abbreviation "nBu" refers to a n-butyl group; the abbreviation "sBu" refers to a sec-butyl group; the abbreviation "tBu" refers to a tertiary butyl group; the abbreviation "N$^Z$-amd" refers to R₁—NC(R₃)N—R₂, wherein R₃=a C1-C6 alkyl group and R₁ and R₂=Z, which is defined as Me, Et, Pr, iPr, nBu, iBu, sBu, or tBu, for example N$^{Me}$-amd is Me-NC(Me)N-Me; the abbreviation "N$^Z$-fmd" refers to R₁—NC(R₃)N—R₂, wherein R₃=H and R₁ and R₂=Z, which is defined as Me, Et, Pr, iPr, or tBu; the abbreviation "N$^Z$-gmd" refers to R₁—NC(R₃)N—R₂ wherein R₃=NR₅R₆ with R₅ and R₆=H or a C1-C6 alkyl group, and R₁ and R₂=Z, which is defined as Me, Et, Pr, iPr, nBu, iBu, sBu, or tBu; the abbreviation "THF" refers to tetrahydrofuran; the abbreviation "TMA" refers to trimethyl aluminum; the abbreviation "ALD" refers to atomic layer deposition; the abbreviation "CVD" refers to chemical vapor deposition; the abbreviation "LPCVD" refers to low pressure chemical vapor deposition; the abbreviation "P-CVD" refers to pulsed chemical vapor deposition; the abbreviation "PE-ALD" refers to plasma enhanced atomic layer deposition; the abbreviation "MIM" refers to Metal Insulator Metal (a structure used in capacitors); the abbreviation "DRAM" refers to dynamic random access memory; the abbreviation "FeRAM" refers to ferroelectric random access memory; the abbreviation "CMOS" refers to complementary metal-oxide-semiconductor; the abbreviation "TGA" refers to thermogravimetric analysis.

The standard abbreviations of the elements from the periodic table of elements are used herein. It should be understood that elements may be referred to by these abbreviations (e.g., Ti refers to titanium, Ba refers to barium, etc.).

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
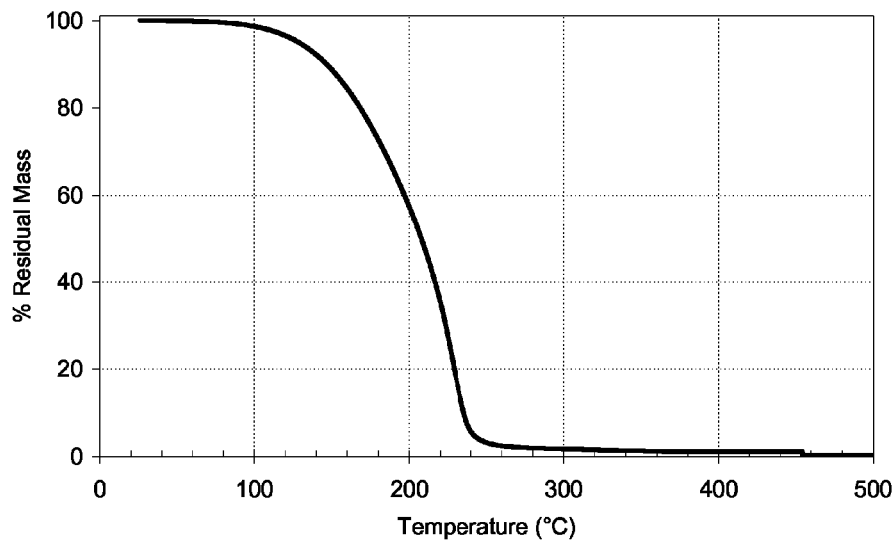
FIG. 1 is a thermogravimetric analysis (TGA) graph demonstrating the percentage of weight loss with temperature change for Ti($N^{iPr}$-amd)(OiPr)$_3$.

Disclosed are novel titanium-containing precursors, methods of synthesizing the same, and methods of using the same.

The disclosed heteroleptic titanium-containing precursors are derived from different classes of ligand systems, such as amidinate, formamidinate, guanidinate, amide, and/or chelating amide ligands, plus alkoxide ligands. Precursor design may help improve volatility, reduce the melting point (liquids or very low melting solids), increase reactivity with water, and increase thermal stability for wider process window applications.

The disclosed titanium-containing precursors have the following formulae:

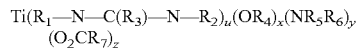

Formula I or

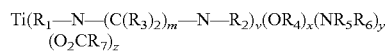

Formula II wherein:
R$_1$, R$_2$, R$_5$, R$_6$, and R$_7$ are independently selected from the group consisting of H and C1-C6 alkyl group;
R$_3$=H, C1-C6 alkyl group, or NMe$_2$;
R$_4$ is a C1-C6 alkyl group;
m=2-4;
u=0-2;
v=0-1;
x=1-3;
y=0-2;
z=0-1;
in Formula I, u+x+y+z=4;
in Formula II, 2v+x+y+z=4; and
u, v, or z≥1.

As defined above, the C1-C6 alkyl group includes any linear, branched, or cyclic alkyl groups having from 1 to 6 carbon atoms, including but not limited to Me, tBu, or cyclohexyl groups.

In Formula I, the R$_1$—NC(R$_3$)N—R$_2$ ligand has the following chemical structure:

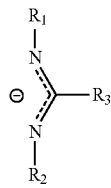

In Formula II, the R$_1$—N—(C(R$_3$)$_2$)$_m$—N—R$_2$ ligand has the following chemical structure:

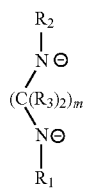

Therefore, although the same elements have been maintained in the backbone of the ligand (i.e., —N—C—N—), the ligand itself has gone from a −1 ligand having one delocalized negative charge between the —N—C—N— backbone to a −2 ligand having a negative charge localized at each nitrogen atom. Additionally, the Formula I ligand has a more rigid structure than the Formula II ligand.

When R$_1$ and R$_3$ are C1-C6 linear or branched alkyl groups in Formula I, R$_1$ and R$_3$ may be independent substituents or they may be linked together to form a monocyclic structure extending from R$_1$ to R$_3$, as demonstrated below.

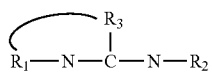

Similarly, when R$_1$, R$_3$ and R$_2$ are C1-C6 linear or branched alkyl groups in Formula I, R$_1$, R$_3$ and R$_2$ may be independent substituents or they may be linked together to form a bicyclic structure, as demonstrated below.

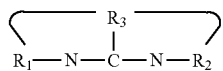

The configuration of the disclosed precursors was selected in order to optimize the reactivity (especially with H$_2$O) and, at the same time, the stability. The Ti—N bond is weak and will react rapidly on the surface. At the same time, the Ti—O bond is much stronger and will help stabilize the molecule to avoid fast decomposition. By tuning this molecule, a precursor is obtained that reacts well on the substrate thanks to a weaker site When u=1, x=3, y=0, and z=0 in Formula I, R$_1$ and R$_2$ are preferably Et or iPr, R$_3$ is preferably H, Me, or NMe$_2$, and R$_4$ is preferably a C1-C4 linear or branched alkyl chain. Exemplary precursors include Ti(iPr—N—C(H)—N-iPr)$_1$(OiPr)$_3$, Ti(iPr—N—C(H)—N-iPr)$_1$(OMe)$_3$, Ti(iPr—N—C(H)—N-iPr)$_1$(OEt)$_3$, Ti(iPr—N—C(H)—N-iPr)$_1$(OnPr)$_3$, Ti(iPr—N—C(H)—N-iPr)$_1$(OsBu)$_3$, Ti(iPr—N—C(H)—N-iPr)$_1$ (OiBu)$_3$, Ti(iPr—N═C(H)—N-iPr)$_1$(OtBu)$_3$, Ti(iPr—N═C(Me)-N-iPr)$_1$(OiPr)$_3$, Ti(iPr—N═C(Me)-N-iPr)$_1$(OMe)$_3$, Ti(iPr—N═C(Me)-N-iPr)$_1$(OEt)$_3$, Ti(iPr—N═C(Me)-N-iPr)$_1$(OnPr)$_3$, Ti(iPr—N═C(Me)-N-iPr)$_1$(OsBu)$_3$, Ti(iPr—N═C(Me)-N-iPr)$_1$(OiBu)$_3$, Ti(iPr—N═C(Me)-N-iPr)$_1$(OtBu)$_3$, Ti(Et-N═C(Me)-N-Et)$_1$(OEt)$_3$, Ti(Et-N═C(Me)-N-Et)$_1$(OMe)$_3$, Ti(Et-N═C(Me)-N-Et)$_1$(OnPr)$_3$, Ti(Et-N═C(Me)-N-Et)$_1$(OsBu)$_3$, Ti(Et-N═C(Me)-N-Et)$_1$(OiBu)$_3$, Ti(Et-N═C(Me)-N-Et)$_1$(OtBu)$_3$, or Ti(iPr—N═C(NMe$_2$)—N-iPr)(OiPr)$_3$. The preferred exemplary precursor is Ti(iPr—N═C(Me)-N-iPr)$_1$(OiPr)$_3$.

When m=2 or 3, v=1, x=2, y=0, and z=0 in Formula II, R$_1$ and R$_2$ are preferably Et or iPr, R$_3$ is preferably H, and R$_4$ is preferably a C1-C4 linear or branched alkyl chain. More preferably, R$_1$ and R$_2$ are not Me when m=2. Exemplary precursors include Ti(iPr—N—(CH$_2$)$_2$—N-iPr)$_1$(OiPr)$_2$, Ti(iPr—N—(CH$_2$)$_2$—N-iPr)$_1$(OMe)$_2$, Ti(iPr—N—(CH$_2$)$_2$—N-iPr)$_1$(OEt)$_2$, Ti(iPr—N—(CH$_2$)$_2$—N-iPr)$_1$(OnPr)$_2$, Ti(iPr—N—(CH$_2$)$_2$—N-iPr)$_1$(OsBu)$_2$, Ti(iPr—N—(CH$_2$)$_2$—N-iPr)$_1$(OiBu)$_2$, Ti(iPr—N—(CH$_2$)$_2$—N-iPr)$_1$(OtBu)$_2$, Ti(Et-N—(CH$_2$)$_2$—N-Et)$_1$(OiPr)$_2$, Ti(Et-N—(CH$_2$)$_2$—N-Et)(OMe)$_2$, Ti(Et-N—(CH$_2$)$_2$—N-Et)$_1$(OEt)$_2$, Ti(Et-N—(CH$_2$)$_2$—N-Et)$_1$(OnPr)$_2$, Ti(Et-N—(CH$_2$)$_2$—N-Et)$_1$(OsBu)$_2$, Ti(Et-N—(CH$_2$)$_2$—N-Et)$_1$(OiBu)$_2$, Ti(Et-N—(CH$_2$)$_2$—N-Et)$_1$(OtBu)$_2$, Ti(iPr—N—(CH$_2$)$_3$—N-iPr)$_1$(OiPr)$_2$, Ti(iPr—N—(CH$_2$)$_3$—N-iPr)$_1$(OMe)$_2$, Ti(iPr—N—(CH$_2$)$_3$—N-iPr)$_1$(OEt)$_2$, Ti(iPr—N—(CH$_2$)$_3$—N-iPr)$_1$(OnPr)$_2$, Ti(iPr—N—(CH$_2$)$_3$—N-iPr)$_1$(OsBu)$_2$, Ti(iPr—N—(CH$_2$)$_3$—N-iPr)$_1$(OiBu)$_2$, Ti(iPr—N—(CH$_2$)$_3$—N-iPr)$_1$(OtBu)$_2$, Ti(Et-N—(CH$_2$)$_3$—N-Et)$_1$(OiPr)$_2$, Ti(Et-N—(CH$_2$)$_3$—N-Et)$_1$(OMe)$_2$, Ti(Et-N—(CH$_2$)$_3$—N-Et)(OEt)$_2$, Ti(Et-N—(CH$_2$)$_3$—N-Et)$_1$(OnPr)$_2$, Ti(Et-N—(CH$_2$)$_3$—N-Et)$_1$(OsBu)$_2$, Ti(Et-N—(CH$_2$)$_3$—N-Et)$_1$(OiBu)$_2$, or Ti(Et-N—(CH$_2$)$_3$—N-Et)$_1$(OtBu)$_2$. The preferred exemplary precursors are Ti(iPr—N—(CH$_2$)$_2$—N-iPr)$_1$(OiPr)$_2$, Ti(Et-N—(CH$_2$)$_3$—N-Et)$_1$(OiPr)$_2$, or Ti(Et-N—(CH$_2$)$_2$—N-Et)$_1$(OiPr)$_2$.

When u=2, x=2, y=0, and z=0 in Formula I, the precursor has the following chemical structure:

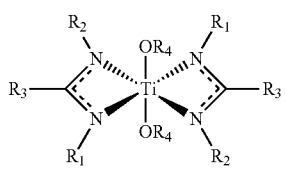

In this embodiment, R$_1$ and R$_2$ are preferably Et or iPr, R$_3$ is preferably H or Me, and R$_4$ is preferably a C1-C4 linear or branched alkyl chain. More preferably, R$_3$ is not NMe$_2$. Exemplary precursors include Ti(iPr—N═C(H)—N-iPr)$_2$(OiPr)$_2$, Ti(iPr—N═C(H)—N-iPr)$_2$(OMe)$_2$, Ti(iPr—N═C(H)—N-iPr)$_2$(OEt)$_2$, Ti(iPr—N═C(H)—N-iPr)$_2$(OnPr)$_2$, Ti(iPr—N═C(H)—N-iPr)$_2$(OsBu)$_2$, Ti(iPr—N═C(H)—N-iPr)$_2$(OiBu)$_2$, Ti(iPr—N═C(H)—N-iPr)$_2$(OtBu)$_2$, Ti(Et-N═C(H)—N-Et)$_2$(OiPr)$_2$, Ti(Et-N═C(H)—N-Et)$_2$(OMe)$_2$, Ti(Et-N═C(H)—N-Et)$_2$(OEt)$_2$, Ti(Et-N═C(H)—N-Et)$_2$(OnPr)$_2$, Ti(Et-N═C(H)—N-Et)$_2$(OsBu)$_2$, Ti(Et-N═C(H)—N-Et)$_2$(OiBu)$_2$, Ti(Et-N═C(H)—N-Et)$_2$(OtBu)$_2$, Ti(iPr—N═C(Me)-N-iPr)$_2$(OiPr)$_2$, Ti(iPr—N═C(Me)-N-iPr)$_2$(OMe)$_2$, Ti(iPr—N═C(Me)-N-iPr)$_2$(OEt)$_2$, Ti(iPr—N═C(Me)-N-iPr)$_2$(OnPr)$_2$, Ti(iPr—N═C(Me)-N-iPr)$_2$(OsBu)$_2$, Ti(iPr—N═C(Me)-N-iPr)$_2$(OiBu)$_2$, Ti(iPr—N═C(Me)-N-iPr)$_2$(OtBu)$_2$, Ti(Et-N═C(Me)-N-Et)$_2$(OiPr)$_2$, Ti(Et-N═C(Me)-N-Et)$_2$(OMe)$_2$, Ti(Et-N═C(Me)-N-Et)$_2$(OEt)$_2$, Ti(Et-N═C(Me)-N-Et)$_2$(OnPr)$_2$, Ti(Et-N═C(Me)-N-Et)$_2$(OsBu)$_2$, Ti(Et-N═C(Me)-N-Et)$_2$(OiBu)$_2$, and Ti(Et-N═C(Me)-N-Et)$_2$(OtBu)$_2$. The preferred exemplary precursor is Ti(iPr—N═C(H)—N-iPr)$_2$(OiPr)$_2$ or Ti(iPr—N═C(Me)-N-iPr)$_2$(OiPr)$_2$.

When u=1, x=2, y=1, and z=0 in Formula I, the precursor has the following chemical structure:

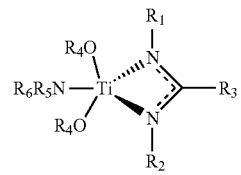

In this embodiment, R$_1$ and R$_2$ are preferably Et or iPr; R$_3$ is preferably H, Me, or NMe$_2$; R$_4$ is preferably iPr; and R$_5$ and R$_6$ preferably are independently Me or Et. Exemplary precursors include Ti(iPr—N═C(Me)-N-iPr)(OiPr)$_2$(NMe$_2$), Ti(iPr—N═C(Me)-N-iPr)(OiPr)$_2$(NEt$_2$), Ti(iPr—N═C(Me)-N-iPr)(OiPr)$_2$(NEtMe), Ti(Et-N═C(Me)-N-Et)(OiPr)$_2$(NMe$_2$), Ti(Et-N═C(Me)-N-Et)(OiPr)$_2$(NEt$_2$), Ti(Et-N═C(Me)-N-Et)(OiPr)$_2$(NEtMe), Ti(iPr—N═C(NMe$_2$)—N-iPr)(OiPr)$_2$(NMe$_2$), Ti(iPr—N═C(NMe$_2$)—N-iPr)(OiPr)$_2$(NEt$_2$), and Ti(iPr—N═C(NMe$_2$)—N-iPr)(OiPr)$_2$(NEtMe). The preferred exemplary precursor is Ti(iPr—N═C(Me)-N-iPr)(OiPr)$_2$(NMe$_2$).

When u=1, x=2, y=0, and z=1 in Formula I, the precursor has the following chemical structure:

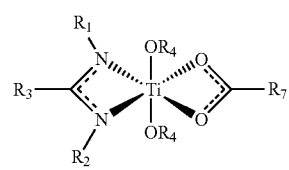

In this embodiment, R$_1$ and R$_2$ are preferably Et or iPr; R$_3$ is preferably H or Me; R$_4$ is preferably iPr; and R$_7$ is preferably Me. Exemplary precursors include Ti(iPr—N═C(Me)-N-iPr)(OiPr)$_2$(O$_2$CMe) and Ti(Et-N═C(Me)-N-Et)(OiPr)$_2$(O$_2$CMe).

When v=1, x=1, y=0, and z=1 in Formula II, the precursor has the following chemical structure:

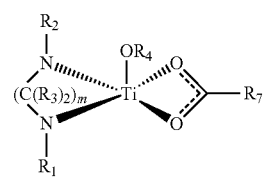

When m=2, v=1, x=1, y=0, z=1, and R$_3$=H, the precursor has the following chemical structure:

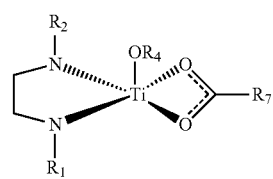

When m=3, v=1, x=1, y=0, z=1, and R₃=H, the precursor has the following chemical structure:

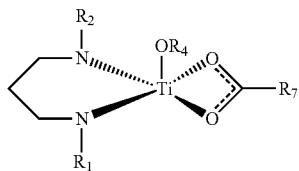

In these embodiments, m is preferably 2 or 3, R₁ and R₂ are preferably Et or iPr; R₃ is preferably H; R₄ is preferably a C1-C4 linear or branched alkyl chain; and R₇ is preferably Me. Exemplary precursors include Ti(iPr—N—(CH₂)₂—N-iPr)(OiPr)(O₂CMe), Ti(iPr—N—(CH₂)₂—N-iPr)(OMe)(O₂CMe), Ti(iPr—N—(CH₂)₂—N-iPr)(OEt)(O₂CMe), Ti(iPr—N—(CH₂)₂—N-iPr)(OnPr)(O₂CMe), Ti(iPr—N—(CH₂)₂—N-iPr)(OsBu)(O₂CMe), Ti(iPr—N—(CH₂)₂—N-iPr)(OiBu)(O₂CMe), Ti(iPr—N—(CH₂)₂—N-iPr)(OtBu)(O₂CMe), Ti(Et-N—(CH₂)₂—N-Et)(OiPr)(O₂CMe), Ti(Et-N—(CH₂)₂—N-Et)(OMe)(O₂CMe), Ti(Et-N—(CH₂)₂—N-Et)(OEt)(O₂CMe), Ti(Et-N—(CH₂)₂—N-Et)(OnPr)(O₂CMe), Ti(Et-N—(CH₂)₂—N-Et)(OsBu)(O₂CMe), Ti(Et-N—(CH₂)₂—N-Et)(OiBu)(O₂CMe), and Ti(Et-N—(CH₂)₂—N-Et)(OtBu)(O₂CMe).

When u=1, x=1, y=2, and z=0 in Formula I, exemplary precursors include Ti(iPr—N—C(Me)-N-iPr)(OiPr)(NMe₂)₂, Ti(iPr—N—C(Me)-N-iPr)(OiPr)(NEt₂)₂, Ti(iPr—N—C(Me)-N-iPr)(OiPr)(NEtMe)₂, Ti(Et-N—C(Me)-N-Et)(OiPr)(NMe₂)₂, Ti(Et-N—C(Me)-N-Et)(OiPr)(NEt₂)₂, Ti(Et-N—C(Me)-N-Et)(OiPr)(NEtMe)₂, Ti(iPr—N—C(NMe₂)—N-iPr)(OiPr)(NMe₂)₂, Ti(iPr—N—C(NMe₂)—N-iPr)(OiPr)(NEt₂)₂, and Ti(iPr—N—C(NMe₂)—N-iPr)(OiPr)(NEtMe)₂.

When v=1, x=1, y=1, and z=0 in Formula II, exemplary precursors include Ti(iPr—N—(CH₂)₂—N-iPr)(OiPr)(NMe₂), Ti(iPr—N—(CH₂)₂—N-iPr)(OiPr)(NEt₂), Ti(iPr—N—(CH₂)₂—N-iPr)(OiPr)(NEtMe), Ti(Et-N—(CH₂)₂—N-Et)(OiPr)(NMe₂), Ti(Et-N—(CH₂)₂—N-Et)(OiPr)(NEt₂), and Ti(Et-N—(CH₂)₂—N-Et)(OiPr)(NEtMe).

When u=1, x=1, y=0, and z=2 in Formula I, exemplary precursors include Ti(iPr—N—C(Me)-N-iPr)(OiPr)(O₂CMe)₂ and Ti(Et-N—C(Me)-N-Et)(OiPr)(O₂CMe)₂.

When u, v, y=0, x=2, and z=2 in either of Formula I or Formula II, exemplary precursors include Ti(OiPr)₂(O₂CMe)₂.

When u, v, y=0, x=3, and z=1 in either of Formula I or Formula II, exemplary precursors include Ti(OiPr)₃(O₂CMe).

The disclosed precursors may be synthesized by combining a hydrocarbon solution of H(R₁—N—C(R₃)—N—R₂) with a neat or hydrocarbon solution of a titanium compound, such as Ti(OR₄)₃(NR₅R₆) or Ti(OR₄)₂(NR₅R₆)₂, under atmosphere of nitrogen, the outlet of the mixing flask being connected to an oil bubbler. Exemplary hydrocarbon solutions include pentane. The resulting solution is stirred at room temperature overnight. Where applicable, HO₂CR₇ may be added and further stirred for 6-12 hours. Solvent and volatiles are removed from the reaction mixture under vacuum. Purification of the resulting liquid or solid is carried out by distillation or sublimation, respectively. Additional synthesis details are provided in the Examples.

Also disclosed are methods of using the disclosed titanium-containing precursors for vapor deposition methods. The disclosed methods provide for the use of the titanium-containing precursors for deposition of titanium-containing films. The disclosed methods may be useful in the manufacture of semiconductor, photovoltaic, LCD-TFT, or flat panel type devices. The method includes: providing a substrate; providing a vapor including at least one of the disclosed titanium-containing precursors: and contacting the vapor with the substrate (and typically directing the vapor to the substrate) to form a titanium-containing layer on at least one surface of the substrate.

The disclosed methods also provide for forming a bimetal-containing layer on a substrate using a vapor deposition process and, more particularly, for deposition of STO or BST films. The disclosed methods may be useful in the manufacture of semiconductor, photovoltaic, LCD-TFT, or flat panel type devices.

The method includes: providing a substrate; providing a vapor including at least one of the disclosed titanium-containing precursors and contacting the vapor with the substrate (and typically directing the vapor to the substrate) to form a bi metal-containing layer on at least one surface of the substrate. An oxygen source, such as O₃, O₂, H₂O, and NO, preferably H₂O, may also be provided with the vapor.

The disclosed titanium-containing precursors may be used to deposit titanium-containing films using any deposition methods known to those of skill in the art. Examples of suitable deposition methods include without limitation, conventional chemical vapor deposition (CVD), low pressure chemical vapor deposition (LPCVD), atomic layer deposition (ALD), pulsed chemical vapor deposition (P-CVD), plasma enhanced atomic layer deposition (PE-ALD), or combinations thereof. Preferably, the deposition method is ALD or PE-ALD.

The vapor of the titanium-containing precursor is introduced into a reaction chamber containing at least one substrate. The temperature and the pressure within the reaction chamber and the temperature of the substrate are held at suitable conditions so that contact between the titanium-containing precursor and substrate results in formation of a Ti-containing layer on at least one surface of the substrate. A reactant may also be used to help in formation of the Ti-containing layer.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reaction chambers are capable of serving as an ALD reaction chamber. The reaction chamber may be maintained at a pressure ranging from about 0.5 mTorr to about 20 Torr. In addition, the temperature within the reaction chamber may range from about 2000° C. to about 600° C. One of ordinary skill in the art will recognize that the temperature may be optimized through mere experimentation to achieve the desired result.

The substrate may be heated to a sufficient temperature to obtain the desired titanium-containing film at a sufficient growth rate and with desired physical state and composition. A non-limiting exemplary temperature range to which the substrate may be heated includes from 150° C. to 600° C. Preferably, the temperature of the substrate remains less than or equal to 450° C.

The type of substrate upon which the titanium-containing film will be deposited will vary depending on the final use intended. In some embodiments, the substrate may be chosen from oxides which are used as dielectric materials in MIM, DRAM, or FeRam technologies (for example, HfO₂ based materials, TiO₂ based materials, ZrO₂ based materials, rare earth oxide based materials, ternary oxide based materials, etc.) or from nitride-based films (for example, TaN) that are used as an oxygen barrier between copper and the low-k layer. Other substrates may be used in the manufacture of semiconductors, photovoltaics, LCD-TFT, or flat panel devices. Examples of such substrates include, but are not limited to, solid substrates such as metal nitride containing substrates (for example, TaN, TiN, WN, TaCN, TiCN, TaSiN, and TiSiN); insulators (for example, $SiO_2$, $Si_3N4$, SiON, $HfO_2$, $Ta_2O_5$, $ZrO_2$, $TiO_2$, $Al_2O_3$, and barium strontium titanate); or other substrates that include any number of combinations of these materials. The actual substrate utilized may also depend upon the specific precursor embodiment utilized. In many instances though, the preferred substrate utilized will be selected from TiN, SRO, Ru, and Si type substrates.

The titanium-containing precursor may be fed in liquid state to a vaporizer where it is vaporized before it is introduced into the reaction chamber. Prior to its vaporization, the titanium-containing precursor may optionally be mixed with one or more solvents, one or more metal sources, and a mixture of one or more solvents and one or more metal sources. The solvents may be selected from the group consisting of toluene, ethyl benzene, xylene, mesitylene, decane, dodecane, octane, hexane, pentane, or others. The resulting concentration may range from approximately 0.05 M to approximately 2 M. The metal source may include any metal-containing precursors now known or later developed.

Alternatively, the titanium-containing precursor may be vaporized by passing a carrier gas into a container containing the titanium-containing precursor or by bubbling the carrier gas into the titanium-containing precursor. The carrier gas and titanium-containing precursor are then introduced into the reaction chamber as a vapor. The carrier gas may include, but is not limited to, Ar, He, $N_2$, and mixtures thereof. The titanium-containing precursor may optionally be mixed in the container with one or more solvents, metal-containing precursors, or mixtures thereof. If necessary, the container may be heated to a temperature that permits the titanium-containing precursor to be in its liquid phase and to have a sufficient vapor pressure. The container may be maintained at temperatures in the range of, for example, 0-150° C. Those skilled in the art recognize that the temperature of the container may be adjusted in a known manner to control the amount of titanium-containing precursor vaporized.

In addition to the optional mixing of the titanium-containing precursor with solvents, metal-containing precursors, and stabilizers prior to introduction into the reaction chamber, the titanium-containing precursor may be mixed with reactants inside the reaction chamber. Exemplary reactants include, without limitation, metal-containing precursors such as strontium-containing precursors, barium-containing cursors, aluminum-containing precursors such as TMA, and any combination thereof. These or other metal-containing precursors may be incorporated into the resultant film in small quantities, as a dopant, or as a second or third metal in the resulting film, such as BST and STO.

When the desired titanium-containing film also contains oxygen, such as, for example and without limitation, STO, the reactants may include an oxygen source which is selected from, but not limited to, $O_2$, $O_3$, $H_2O$, $H_2O_2$, acetic acid, formalin, para-formaldehyde, and combinations thereof. Preferably, when an ALD process is performed, the reactant is $H_2O$.

When the desired titanium-containing film also contains another metal, such as, for example and without limitation, Ta, Hf, Zr, Nb, Mg, Al, Sr, Y, Ba, Ca, As, Sb, Bi, Sn, Pb, Co, lanthanides (such as Eu), or combinations thereof, the reactants may include a metal-containing precursor which is selected from, but not limited to, metal alkyls, such as $Ln(RCp)_3$ or $Co(RCp)_2$, metal amines, such as $Zr(Cp)(NMe_2)_3$ or $Hf(Cp)(NMe_2)_3$, and any combination thereof.

In one preferred embodiment, the reactant may be a metal-containing precursor compound having the formula $M(L)_2$ or $M(L)_2.A$, wherein M is Sr or Ba, L is selected from (a) substituted cyclopentadienyl ligand systems $(R_1R_2R_3R_4R_5Cp)$ in which each of $R_1$ to $R_5$ is independently selected from H or C1-C6 linear or branched alkyl chains, or (b) beta-diketonate ligand systems (—O—$CR_6$—CH—$CR_7$—O—), in which each of $R_6$ and $R_7$ is independently selected from C1-C6 linear or branched alkyl chain; and A=is a neutral oxygen containing molecule, including but not limited to tetrahydrofuran, dimethoxyethane, diglyme, triglyme, tetraglyme, or a combination thereof. Preferably, the metal-containing precursor has the formula $M(R_5Cp)_2$ with each R being independently selected from H, Me, Et, and nBu.

Exemplary metal-containing precursors include but are not limited to $Sr(iPr_3Cp)_2$, $Sr(iPr_3Cp)_2.thf$, $Sr(iPr_3Cp)_2.dme$, $Sr(tBu_3Cp)_2$, $Sr(tBu_3Cp)_2.thf$, $Sr(tBu_3Cp)_2.dme$, $Sr(thmd)_2$, $Sr(thmd)_2.triglyme$, $Sr(thmd)_2.tetraglyme$, $Sr(MesCp)_2$, $Sr(Me_4Cp)_2$, $Sr(Me_4EtCp)_2$, $Sr(Me_4nBuCp)_2$, $Ba(iPr_3Cp)_2$, $Ba(iPr_3Cp)_2.thf$, $Ba(iPr_3Cp)_2.dme$, $Ba(tBu_3Cp)_2$, $Ba(tBu_3Cp)_2.thf$, $Ba(tBu_3Cp)_2.dme$, $Ba(thmd)_2$, $Ba(thmd)_2.triglyme$, $Ba(thmd)_2.tetraglyme$, $Ba(MesCp)_2$, $Ba(Me_4Cp)_2$, $Ba(Me_4EtCp)_2$, and $Ba(Me_4nBuCp)_2$.

The vapor of the metal-containing precursor (i.e., second vapor) is introduced into a reaction chamber. The temperature and the pressure within the reaction chamber and the temperature of the substrate are held at suitable conditions so that contact between the metal-containing precursor and substrate results in formation of a M-containing layer on at least one surface of the substrate. A reactant may also be used to help in formation of the M-containing layer.

One of ordinary skill in the art will recognize that additional reactants may be used in the disclosed deposition processes. The term "second vapor" is merely used to avoid confusion with the "vapor" of the titanium-containing precursor. For example, a second vapor of a metal-containing precursor having the formula $Sr(iPr_3Cp)_2$ and a third vapor of a metal-containing precursor having the formula $Ba(MesCp)_2$ may be used with the vapor of the disclosed titanium-containing precursors to form a BST film.

The titanium-containing precursor and one or more reactants may be introduced into the reaction chamber simultaneously (chemical vapor deposition), sequentially (atomic layer deposition), or in other combinations. For example, the titanium-containing precursor may be introduced in one pulse and two additional metal sources may be introduced together in a separate pulse [modified atomic layer deposition]. Alternatively, the reaction chamber may already contain the reactant prior to introduction of the titanium-containing precursor. The reactant may be passed through a plasma system localized remotely from the reaction chamber, and decomposed to radicals. Alternatively, the titanium-containing precursor may be introduced to the reaction chamber continuously while other metal sources are introduced by pulse (pulsed-chemical vapor deposition). In each example, a pulse may be followed by a purge or evacuation step to remove excess amounts of the component introduced. In each example, the pulse may last for a time period ranging from about 0.01 s to about 10 s, alternatively from about 0.3 s to about 3 s, alternatively from about 0.5 s to about 2 s.

In one non-limiting exemplary atomic layer deposition type process, the vapor phase of a titanium-containing precursor is introduced into the reaction chamber, where it is contacted with a suitable substrate. Excess titanium-containing precursor may then be removed from the reaction chamber by purging and/or evacuating the reaction chamber. An oxygen source is introduced into the reaction chamber where it reacts with the absorbed titanium precursor in a self-limiting manner. Any excess oxygen source is removed from the reaction chamber by purging and/or evacuating the reaction chamber. If the desired film is a titanium oxide film, this two-step process may provide the desired film thickness or may be repeated until a film having the necessary thickness has been obtained.

Alternatively, if the desired film is a titanium metal oxide film (i.e., TiM), the two-step process above may be followed by introduction of a second vapor of a metal-containing precursor into the reaction chamber. The metal-containing precursor will be selected based on the nature of the titanium metal oxide film being deposited. After introduction into the reaction chamber, the metal-containing precursor is contacted with the substrate. Any excess metal-containing precursor is removed from the reaction chamber by purging and/or evacuating the reaction chamber. Once again, an oxygen source may be introduced into the reaction chamber to react with the metal-containing precursor. Excess oxygen source is removed from the reaction chamber by purging and/or evacuating the reaction chamber. If a desired film thickness has been achieved, the process may be terminated. However, if a thicker film is desired, the entire four-step process may be repeated. By alternating the provision of the titanium-containing precursor, metal-containing precursor, and oxygen source, a film of desired composition and thickness can be deposited.

Additionally, by varying the number of pulses, films having a desired stoichiometric M:Ti ratio may be obtained. For example, a $Sr_2TiO_4$ film may be obtained by having one pulse of the titanium-containing precursor and two pulses of the metal-containing precursor, with each pulse being followed by pulses of the oxygen source. However, one of ordinary skill in the art will recognize that the number of pulses required to obtain the desired film may not be identical to the stoichiometric ratio of the resulting film.

The titanium-containing films or titanium-containing layers resulting from the processes discussed above may include STO, BST, or PZT. One of ordinary skill in the art will recognize that by judicial selection of the appropriate titanium-containing precursor and reactants, the desired film composition may be obtained.

EXAMPLES

The following non-limiting examples are provided to further illustrate embodiments of the invention. However, the examples are not intended to be all inclusive and are not intended to limit the scope of the inventions described herein.

Example 1

$Ti(N^{iPr}\text{-amd})(OiPr)_3$: A 200 mL pentane solution was chilled to −30° C. for 1 h, followed by addition of 10.0 g, 37.15 mmol, of $Ti(OiPr)_3(NMe_2)$ and stirring at room temperature under atmosphere of nitrogen. A solution of $N^{iPr}$-amd-H (5.28 g, 37.15 mmol) in 20 mL of pentane was added slowly to the above mixture. The outlet of the flask was connected to an oil bubbler, which in turn was connected to an acid scrubber. The resulting solution was stirred at room temperature overnight. Solvent and volatiles were removed from the reaction mixture under vacuum, resulting in an orange liquid. Purification of the orange liquid by distillation gave 12.5 g (92%). FIG. 1 is a TGA graph demonstrating the percentage of weight loss with temperature change for this precursor. NMR ($C_6D6$, δ): 1.17 (12H, d, $(CH_3)_2$—CH—N—$C(CH_3)$=N—CH—$(CH_3)_2$), 1.23 (18H, d, O—CH—$(CH_3)_2$), 1.86 (3H, s, $(CH_3)_2$—CH—N—$C(CH_3)$=N—CH—$(CH_3)_2$), 3.57 (1H, m, O—CH—$(CH_3)_2$), 4.46 (2H, m, O—CH—$(CH_3)_2$), 4.73 (2H, m, $(CH_3)_2$—CH—N—C(H)=N—CH—$(CH_3)_2$).

Example 2

Figure 2:
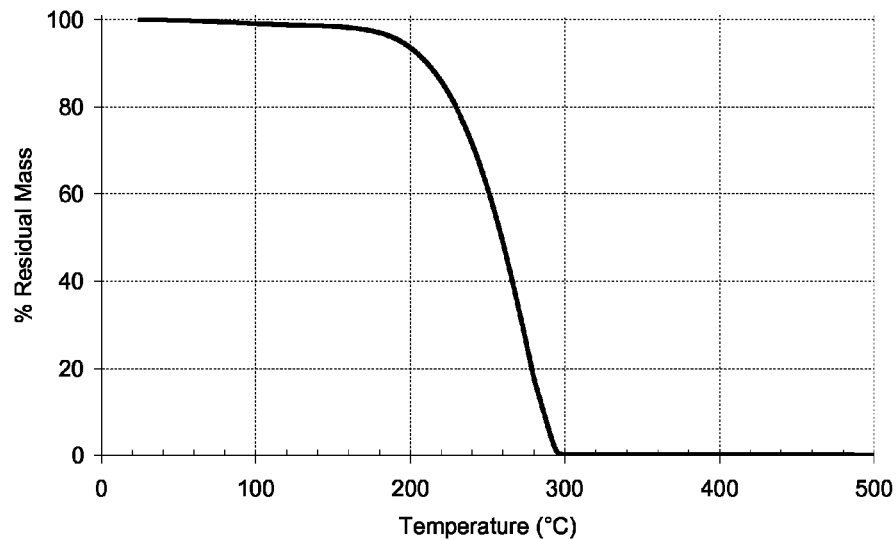
FIG. 2 is a TGA graph for Ti($N^{iPr}$-amd)$_2$(OiPr)$_2$.

$Ti(NiPr\text{-amd})_2(OiPr)_2$: To a pentane solution containing 11.19 g, 78.68 mmol, of $N^{iPr}$-amd-H stirring at room temperature was added slowly a neat $Ti(OiPr)_2(NMe_2)_2$ (10.00 g, 39.34 mmol) compound under atmosphere of nitrogen, the outlet of the flask connected to an oil bubbler. The resulting solution was stirred at room temperature overnight. Solvent and volatiles were removed from the reaction mixture under vacuum. A dark orange-red solid was obtained. Purification of the solid was carried out by sublimation, resulting in yield: 15.4 g, 88%. FIG. 2 is a TGA graph demonstrating the percentage of weight loss with temperature change for this precursor.

NMR ($C_6D6$, δ): 1.14 (6H, br, $(CH_3)_2$—CH—N—$C(CH_3)$=N—CH—$(CH_3)_2$), 1.31 (24H, br, $(CH_3)_2$—CH—N—C(H)=N—CH—$(CH_3)_2$), 1.53 (12H, d, O—CH—$(CH_3)_2$), 3.56 (4H, br, $(CH_3)_2$—CH—N—C(H)=N—CH—$(CH_3)_2$), 4.85 (2H, d, O—CH—$(CH_3)_2$).

Example 3

Figure 3:
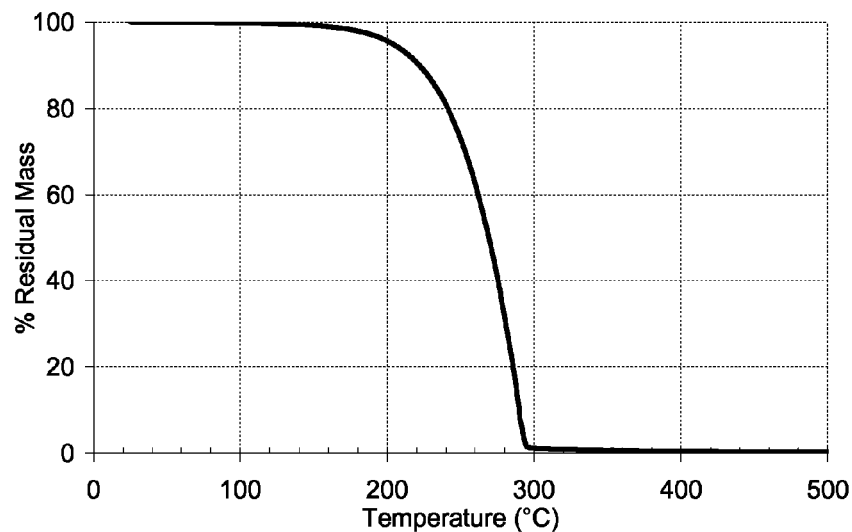
FIG. 3 is a TGA graph for Ti($N^{iPr}$-fmd)$_2$(OiPr)$_2$.

$Ti(N^{iPr}\text{-fmd})_2(OiPr)_2$: To a pentane solution containing 10.00 g, 78.68 mmol, of $N^{iPr}$-fmd-H stirring at room temperature was added slowly a neat $Ti(OiPr)_2(NMe_2)_2$ (10.00 g, 39.34 mmol) compound under atmosphere of nitrogen, the outlet of the flask connected to an oil bubbler. The resulting solution was stirred at room temperature overnight. Solvent and volatiles were removed from the reaction mixture under vacuum. A yellow orange solid was obtained. Purification of the solid was carried out by sublimation, resulting in yield: 16.5 g, 74%. FIG. 3 is a TGA graph demonstrating the percentage of weight loss with temperature change for this precursor.

NMR ($C_6D6$, δ): 1.27 (24H, br, $(CH_3)_2$—CH—N—C(H)=N—CH—$(CH_3)_2$), 1.29 (12H, d, O—CH—$(CH_3)_2$), 3.99 (4H, br, $(CH_3)_2$—CH—N—C(H)=N—CH—$(CH_3)_2$), 4.88 (2H, d, O—CH—$(CH_3)_2$), 7.88 (2H, br, $(CH_3)_2$—CH—N—C(H)=N—CH—$(CH_3)_2$).

Example 4

$Ti(N^{iPr}\text{-gmd})_2(OiPr)_2$: To a pentane solution containing 2.98 g, 23.60 mmol, of iPr—N=C=N-iPr stirring at room temperature was added slowly a neat $Ti(OiPr)_2(NMe_2)_2$ (3.00 g, 11.80 mmol) compound under atmosphere of nitrogen, the outlet of the flask connected to an oil bubbler. The resulting solution was stirred at room temperature overnight. Solvent and volatiles were removed from the reaction mixture under vacuum. A red solid was obtained. Purification of the solid was carried out by sublimation, resulting in very low yield, NMR spectra showed a mixture of products.

Example 5

Figure 4:
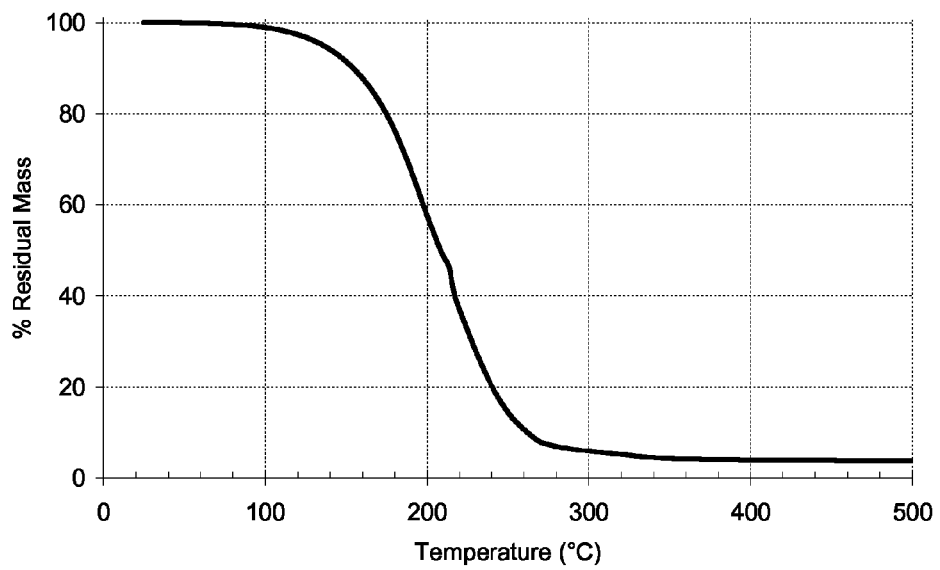
FIG. 4 is a TGA graph for Ti($N^{iPr}$-amd)(OiPr)$_2$(NMe$_2$)

$Ti(N^{iPr}\text{-amd})(OiPr)_2(NMe_2)$: To an 80 mL pentane solution containing 14.3 g, 56.31 mmol of $Ti(OiPr)_2(NMe_2)_2$ stirring at room temperature under atmosphere of nitrogen was added slowly drop wise a solution of Ni$^{Pr}$-amd-H (8.01 g, 56.31 mmol) in 50 mL pentane. The outlet of the flask connected to an oil bubbler, which in turn was connected to an acid scrubber. The resulting solution was stirred at room temperature overnight. Solvent and volatiles were removed from the reaction mixture under vacuum, resulting in an orange red liquid. Purification of orange red liquid by distillation gave 11.5 g (60%). FIG. 4 is a TGA graph demonstrating the percentage of weight loss with temperature change for this precursor. NMR (C$_6$D6, δ): 1.14 (12H, d, (CH$_3$)$_2$—CH—N—C(CH$_3$)=N—CH—(CH$_3$)$_2$), 1.33 (12H, d, O—CH—(CH$_3$)$_2$), 1.47 (3H, s, (CH$_3$)$_2$—CH—N—C(CH$_3$)=N—CH—(CH$_3$)$_2$), 3.37 (6H, s, N(CH$_3$)$_2$) 3.46 (2H, m, O—CH—(CH$_3$)$_2$), 4.82 (2H, m, (CH$_3$)$_2$—CH—N—C(H)=N—CH—(CH$_3$)$_2$).

Example 6

Figure 5:
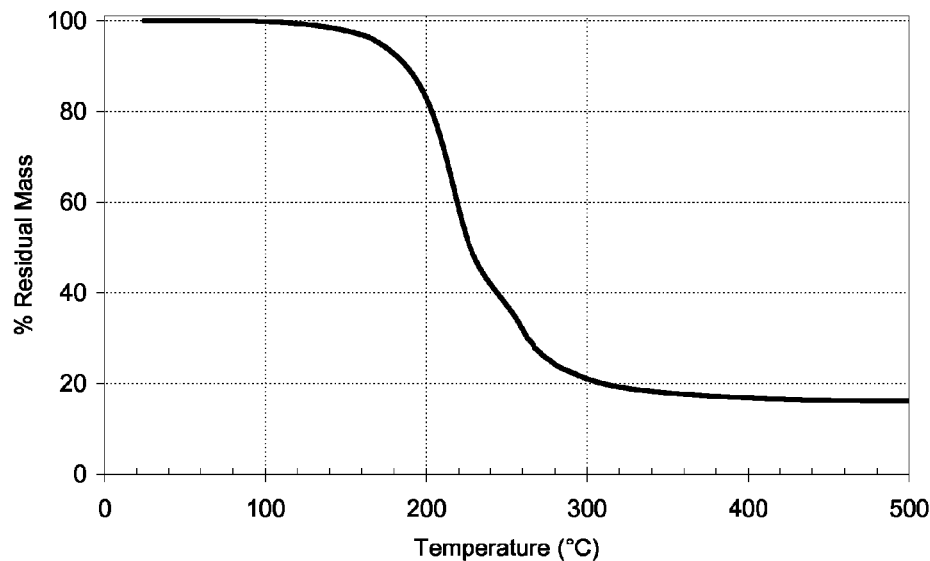
FIG. 5 is a TGA graph for Ti(Et—N—(CH$_2$)$_2$—N-Et)(OiPr)$_2$.

Ti(Et-N—(CH$_2$)$_2$—N-Et)(OiPr)$_2$: To a 60 mL pentane solution containing 15.0 g, 59.01 mmol, of Ti(OiPr)$_2$(NMe$_2$)$_2$ stirring at room temperature under atmosphere of nitrogen was added slowly drop wise neat liquid of Et-NH—(CH$_2$)$_2$—NH-Et (6.86 g, 59.01 mmol). The outlet of the flask was connected to an oil bubbler, which in turn was connected to an acid scrubber. The resulting solution was stirred at room temperature overnight. Solvent and volatiles were removed from the reaction mixture under vacuum, resulting in an orange red liquid. Purification of orange red liquid by distillation resulted in a quantitative yield. FIG. 5 is a TGA graph demonstrating the percentage of weight loss with temperature change for this precursor.

NMR (C$_6$D6, δ): 1.20 (6H, t, CH$_3$—CH$_2$—N—CH$_2$—CH$_2$—N—CH$_2$—CH$_3$), 1.3 (12H, d, O—CH—(CH$_3$)$_2$), 3.5 (4H, s, CH$_3$—CH$_2$—N—CH$_2$—CH$_2$—N—CH$_2$—CH$_3$), 3.7 (4H, q, (CH$_3$—CH$_2$—N—CH$_2$—CH$_2$—N—CH$_2$—CH$_3$), 4.7 (2H, m, O—CH—(CH$_3$)$_2$.

Example 7

Ti(Me-N—(CH$_2$)$_2$—N-Me)(OiPr)$_2$: Synthesis was carried out similar to Example 6. Purification of a red liquid by distillation resulted in decomposition of compound.

NMR (C$_6$D6, δ): 1.31 (12H, d, O—CH—(CH$_3$)$_2$), 3.29 (6H, t, CH$_3$—N—CH$_2$—CH$_2$—N—CH$_3$), 3.41 (4H, s, CH$_3$—N—CH$_2$—CH$_2$—N—CH$_3$), 4.73 (2H, m, O—CH—(CH$_3$)$_2$.

Example 8

Figure 6:
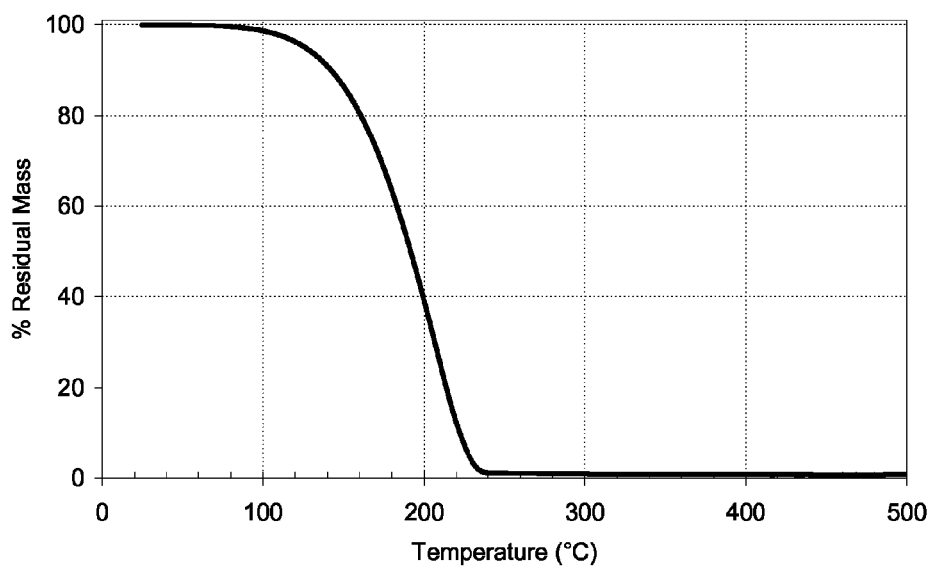
FIG. 6 is a TGA graph for Ti(Me$_2$CH—N—(CH$_2$)$_3$—N—CHMe$_2$)(OiPr)$_2$.

Ti(Me$_2$CH—N—(CH$_2$)$_3$—N—CHMe$_2$)(OiPr)$_2$: Synthesis was carried out similar to Example 6. FIG. 6 is a TGA graph demonstrating the percentage of weight loss with temperature change for this precursor.

NMR (C$_6$D6, δ): 1.20 (6H, t, CH$_3$—CH$_2$—N—CH$_2$—CH$_2$—CH$_2$—N—CH$_2$—CH$_3$), 1.27 (12H, d, O—CH—(CH$_3$)$_2$), 2.23 (2H, br, CH$_3$—CH$_2$—N—CH$_2$—CH$_2$—CH$_2$—N—CH$_2$—CH$_3$), 3.28 (4H, q, (CH$_3$—CH$_2$—N—CH$_2$—CH$_2$—CH$_2$—N—CH$_2$—CH$_3$), 3.33 (4H, q, (CH$_3$—CH$_2$—N—CH$_2$—CH$_2$—CH$_2$—N—CH$_2$—CH$_3$), 4.55 (2H, m, O—CH—(CH$_3$)$_2$.

Example 9

The titanium-containing precursor of Example 1, Ti(N$^{iPr}$-amd)(OiPr)$_3$, and the reactant O$_3$ were used to deposit a film of TiO$_2$ on a SiO$_2$/Si substrate. The SiO$_2$/Si substrate was maintained at a temperature of 250° C. The precursor was vaporized in a bubbler maintained at 50° C. The ALD cycle included a precursor pulse of 5 seconds, followed by a 5 second purge, followed by a reactant pulse of 2 seconds, followed by a 5 second purge. The TiO$_2$ growth rate was observed to be 0.1 Å/cycle. The ALD regime was assessed up to 350° C. with a deposition rate as high as 0.3 Å/cycle.

Example 10

The titanium-containing precursor of Example 1, Ti(N$^{iPr}$-amd)(OiPr)$_3$, and the reactant H$_2$O were used to deposit a film of TiO$_2$ on a SiO$_2$/Si substrate. The SiO$_2$/Si substrate was maintained at a temperature of 250° C. The precursor was vaporized in a bubbler maintained at 50° C. The ALD cycle included a precursor pulse of 20 seconds, followed by a 5 second purge, followed by a reactant pulse of 2 seconds, followed by a 10 second purge. The TiO$_2$ growth rate was observed to be 0.33 Å/cycle. The ALD regime was assessed up to 350° C. with a deposition rate as high as 0.40 Å/cycle.

Example 11

The titanium-containing precursor of Example 2, Ti(N$^{iPr}$-amd)$_2$(OiPr)$_2$, and the reactant O$_3$ were used to deposit a film of TiO$_2$ on a SiO$_2$/Si substrate. The SiO$_2$/Si substrate was maintained at a temperature of 300° C. The orange red precursor was vaporized in a bubbler maintained at 120° C. The ALD cycle included a precursor pulse of 10 seconds, followed by a 5 second purge, followed by a reactant pulse of 2 seconds, followed by a 10 second purge. The TiO$_2$ growth rate was observed to be 0.33 Å/cycle. The ALD regime was assessed up to 325° C. with a deposition rate as high as 0.40 Å/cycle.

Example 12

The titanium-containing precursor of Example 2, Ti(N$^{iPr}$-amd)$_2$(OiPr)$_2$, and the reactant H$_2$O were used to deposit a film of TiO$_2$ on a SiO$_2$/Si substrate. The SiO$_2$/Si substrate was maintained at a temperature of 275° C. The orange red precursor was vaporized in a bubbler maintained at 120° C. The ALD cycle included a precursor pulse of 10 seconds, followed by a 5 second purge, followed by a reactant pulse of 2 seconds, followed by a 5 second purge. The TiO$_2$ growth rate was observed to be 0.40 Å/cycle. The ALD regime was assessed up to 325° C. with a deposition rate as high as 0.47 Å/cycle.

Example 13

The titanium-containing precursor of Example 5, Ti(N$^{iPr}$-amd)(OiPr)$_2$(NMe$_2$), and the reactant O$_3$ were used to deposit a film of TiO$_2$ on a SiO$_2$/Si substrate. The SiO$_2$/Si substrate was maintained at a temperature of 225° C. The orange red precursor was vaporized in a bubbler maintained at 55° C. The ALD cycle included a precursor pulse of 15 seconds, followed by a 5 second purge, followed by a reactant pulse of 2 seconds, followed by a 5 second purge. The TiO$_2$ growth rate was observed to be 0.17 Å/cycle. The ALD regime was assessed up to 375° C. with a deposition rate as high as 0.70 Å/cycle.

Example 14

The titanium-containing precursor of Example 5, Ti(N$^{iPr}$-amd)(OiPr)$_2$(NMe$_2$), and the reactant H$_2$O were used to deposit a film of TiO$_2$ on a SiO$_2$/Si substrate. The SiO$_2$/Si substrate was maintained at a temperature of 225° C. The orange red precursor was vaporized in a bubbler maintained at 55° C. The ALD cycle included a precursor pulse of 10 seconds, followed by a 10 second purge, followed by a reactant pulse of 1 second, followed by a 10 second purge. The $TiO_2$ growth rate was observed to be 0.73 Å/cycle. The ALD regime was assessed up to 375° C. with a deposition rate as high as 0.80 Å/cycle.

Example 15

The titanium-containing precursor of Example 6, Ti(Et-N—($CH_2$)$_2$—N-Et)(OiPr)$_2$, and the reactant $O_3$ were used to deposit a film of $TiO_2$ on a $SiO_2$/Si substrate. The $SiO_2$/Si substrate was maintained at a temperature of 250° C. The precursor was vaporized in a bubbler maintained at 50° C. The ALD cycle included a precursor pulse of 15 seconds, followed by a 5 second purge, followed by a reactant pulse of 2 seconds, followed by a 5 second purge. The $TiO_2$ growth rate was observed to be 0.1 Å/cycle. The ALD regime was assessed up to 325° C. with a deposition rate as high as 0.3 Å/cycle.

Example 16

The titanium-containing precursor of Example 8, Ti($Me_2$CH—N—($CH_2$)$_3$—N—$CHMe_2$)(OiPr)$_2$, and the reactant $O_3$ were used to deposit a film of $TiO_2$ on a $SiO_2$/Si substrate. The $SiO_2$/Si substrate was maintained at a temperature of 250° C. The precursor was vaporized in a bubbler maintained at 50° C. The ALD cycle included a precursor pulse of 15 seconds, followed by a 5 second purge, followed by a reactant pulse of 2 seconds, followed by a 5 second purge. The $TiO_2$ growth rate was observed to be 0.2 Å/cycle. The ALD regime was assessed up to 325° C. with a deposition rate as high as 0.33 Å/cycle.

Example 17

A titanium-containing precursor having the formula Ti(OiPr)$_2$($NMe_2$)$_2$, and the reactant $O_3$ were used to deposit a film of $TiO_2$ on a $SiO_2$/Si substrate. The $SiO_2$/Si substrate was maintained at a temperature of 250° C. The precursor was vaporized in a bubbler maintained at 30° C. The ALD cycle included a precursor pulse of 10 seconds, followed by a 5 second purge, followed by a reactant pulse of 2 seconds, followed by a 5 second purge. The $TiO_2$ growth rate was observed to be 0.77 Å/cycle. The ALD regime was assessed up to 275° C. with a deposition rate as high as 0.77 Å/cycle.

Example 18

The titanium-containing precursor of Example 12, Ti(OiPr)$_2$($NMe_2$)$_2$, and the reactant $H_2O$ were used to deposit a film of $TiO_2$ on a $SiO_2$/Si substrate. The $SiO_2$/Si substrate was maintained at a temperature of 250° C. The precursor was vaporized in a bubbler maintained at 30° C. The ALD cycle included a precursor pulse of 7 seconds, followed by a 5 second purge, followed by a reactant pulse of 2 seconds, followed by a 10 second purge. The $TiO_2$ growth rate was observed to be 0.25 Å/cycle. The ALD regime was assessed up to 275° C. with a deposition rate as high as 0.40 Å/cycle.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A molecule having the following formula:

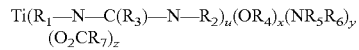

Formula I wherein:
R$_1$, R$_2$, R$_5$, R$_6$, and R$_7$ are independently selected from the group consisting of H and C1-C6 alkyl group;
R$_3$=H, C1-C6 alkyl group, or $NMe_2$;
R$_4$ is a C1-C6 alkyl group;
u=2;
x=2;
y=0; and
z=0.

2. The molecule of claim 1, wherein R$_1$ and R$_2$ are independently Et or iPr, R$_3$ is H or Me, and R$_4$ is a C1-C4 linear or branched alkyl chain.

3. The molecule of claim 1, wherein the molecule is selected from the group consisting of Ti(iPr—N—C(H)—N-iPr)$_2$(OiPr)$_2$, Ti(iPr—N—C(H)—N-iPr)$_2$(OMe)$_2$, Ti(iPr—N—C(H)—N-iPr)$_2$(OEt)$_2$, Ti(iPr—N—C(H)—N-iPr)$_2$(OnPr)$_2$, Ti(iPr—N—C(H)—N-iPr)$_2$(OsBu)$_2$, Ti(iPr—N—C(H)—N-iPr)$_2$(OiBu)$_2$, Ti(iPr—N—C(H)—N-iPr)$_2$(OtBu)$_2$, Ti(Et-N—C(H)—N-Et)$_2$(OiPr)$_2$, Ti(Et-N—C(H)—N-Et)$_2$(OMe)$_2$, Ti(Et-N—C(H)—N-Et)$_2$(OEt)$_2$, Ti(Et-N—C(H)—N-Et)$_2$(OnPr)$_2$, Ti(Et-N—C(H)—N-Et)$_2$(OsBu)$_2$, Ti(Et-N—C(H)—N-Et)$_2$(OiBu)$_2$, Ti(Et-N—C(H)—N-Et)$_2$(OtBu)$_2$, Ti(iPr—N—C(Me)-N-iPr)$_2$(OiPr)$_2$, Ti(iPr—N—C(Me)-N-iPr)$_2$(OMe)$_2$, Ti(iPr—N—C(Me)-N-iPr)$_2$(OEt)$_2$, Ti(iPr—N—C(Me)-N-iPr)$_2$(OnPr)$_2$, Ti(iPr—N—C(Me)-N-iPr)$_2$(OsBu)$_2$, Ti(iPr—N—C(Me)-N-iPr)$_2$(OiBu)$_2$, Ti(iPr—N—C(Me)-N-iPr)$_2$(OtBu)$_2$, Ti(Et-N—C(Me)-N-Et)$_2$(OiPr)$_2$, Ti(Et-N—C(Me)-N-Et)$_2$(OMe)$_2$, Ti(Et-N—C(Me)-N-Et)$_2$(OEt)$_2$, Ti(Et-N—C(Me)-N-Et)$_2$(OnPr)$_2$, Ti(Et-N—C(Me)-N-Et)$_2$(OsBu)$_2$, Ti(Et-N—C(Me)-N-Et)$_2$(OiBu)$_2$, and Ti(Et-N—C(Me)-N-Et)$_2$(OtBu)$_2$.

4. The molecule of claim 3, wherein the molecule is Ti(iPr—N—C(H)—N-iPr)$_2$(OiPr)$_2$ or Ti(iPr—N—C(Me)-N-iPr)$_2$(OiPr)$_2$.

5. A method of forming a Ti-containing layer on a substrate, the method comprising:
providing a reaction chamber having at least one substrate disposed therein;
introducing into the reaction chamber a vapor including at least one precursor having the formula:

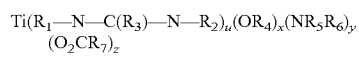

Formula I wherein:
R$_1$, R$_2$, R$_5$, R$_6$, and R$_7$ are independently selected from the group consisting of H and C1-C6 alkyl group;
R$_3$=H, C1-C6 alkyl group, or $NMe_2$;
R$_4$ is a C1-C6 alkyl group;
u=2;
x=2;
y=0; and
z=0;
contacting the vapor with the substrate to form a Ti-containing layer on at least one surface of the substrate using a vapor deposition process.

6. The method of claim 5, wherein R$_1$ and R$_2$ are independently Et or iPr, R$_3$ is H or Me, and R$_4$ is a C1-C4 linear or branched alkyl chain.

7. The method of claim 5, wherein the at least one precursor is selected from the group consisting of Ti(iPr—N═C(H)—N-iPr)$_2$(OiPr)$_2$, Ti(iPr—N═C(H)—N-iPr)$_2$(OMe)$_2$, Ti(iPr—N═C(H)—N-iPr)$_2$(OEt)$_2$, Ti(iPr—N═C(H)—N-iPr)$_2$(OnPr)$_2$, Ti(iPr—N═C(H)—N-iPr)$_2$(OsBu)$_2$, Ti(iPr—N═C(H)—N-iPr)$_2$(OiBu)$_2$, Ti(iPr—N═C(H)—N-iPr)$_2$(OtBu)$_2$, Ti(Et-N═C(H)—N-Et)$_2$(OiPr)$_2$, Ti(Et-N═C(H)—N-Et)$_2$(OMe)$_2$, Ti(Et-N═C(H)—N-Et)$_2$(OEt)$_2$, Ti(Et-N═C(H)—N-Et)$_2$(OnPr)$_2$, Ti(Et-N═C(H)—N-Et)$_2$(OsBu)$_2$, Ti(Et-N═C(H)—N-Et)$_2$(OiBu)$_2$, Ti(Et-N═C(H)—N-Et)$_2$(OtBu)$_2$, Ti(iPr—N═C(Me)-N-iPr)$_2$(OiPr)$_2$, Ti(iPr—N═C(Me)-N-iPr)$_2$(OMe)$_2$, Ti(iPr—N═C(Me)-N-iPr)$_2$(OEt)$_2$, Ti(iPr—N═C(Me)-N-iPr)$_2$(OnPr)$_2$, Ti(iPr—N═C(Me)-N-iPr)$_2$(OsBu)$_2$, Ti(iPr—N═C(Me)-N-iPr)$_2$(OiBu)$_2$, Ti(iPr—N═C(Me)-N-iPr)$_2$(OtBu)$_2$, Ti(Et-N═C(Me)-N-Et)$_2$(OiPr)$_2$, Ti(Et-N═C(Me)-N-Et)$_2$(OMe)$_2$, Ti(Et-N═C(Me)-N-Et)$_2$(OEt)$_2$, Ti(Et-N═C(Me)-N-Et)$_2$(OnPr)$_2$, Ti(Et-N═C(Me)-N-Et)$_2$(OsBu)$_2$, Ti(Et-N═C(Me)-N-Et)$_2$(OiBu)$_2$, and Ti(Et-N═C(Me)-N-Et)$_2$(OtBu)$_2$.

8. The method of claim 7, wherein the molecule is Ti(iPr—N═C(H)—N-iPr)$_2$(OiPr)$_2$ or Ti(iPr—N═C(Me)-N-iPr)$_2$(OiPr)$_2$.

9. The method of claim 7, further comprising:
   introducing into the reaction chamber a second vapor including at least one metal-containing precursor selected from the group consisting of M(L)$_2$ and M(L)$_2$.A, wherein:
   M is Sr or Ba;
   L is selected from substituted cyclopentadenyl ligand systems R$_1$R$_2$R$_3$R$_4$R$_5$Cp or beta-diketonate ligand systems —O—CR$_6$—CH—CR$_7$—O—;
   each of R$_1$ to R$_5$ is independently selected from H or C1-C6 linear or branched alkyl chain;
   each of R$_6$ and R$_7$ is independently selected from C1-C6 linear or branched alkyl chain; and
   A is a neutral oxygen containing molecules selected from the group consisting of tetrahydrofuran, dimethoxyethane, diglyme, triglyme, and tetraglyme; and
   contacting the second vapor with the substrate to form a metal-containing layer on at least one surface of the substrate using the vapor deposition process.

10. The method of claim 9, wherein the metal-containing precursor is selected from the group consisting of Sr(iPr$_3$Cp)$_2$, Sr(iPr$_3$Cp)$_2$.thf, Sr(iPr$_3$Cp)$_2$.dme, Sr(tBu$_3$Cp)$_2$, Sr(tBu$_3$Cp)$_2$.thf, Sr(tBu$_3$Cp)$_2$.dme, Sr(thmd)$_2$, Sr(thmd)$_2$.triglyme, Sr(thmd)$_2$.tetraglyme, Sr(Me$_5$Cp)$_2$, Sr(Me$_4$Cp)$_2$, Sr(Me$_4$EtCp)$_2$, Sr(Me$_4$nBuCp)$_2$, Ba(iPr$_3$Cp)$_2$, Ba(iPr$_3$Cp)$_2$.thf, Ba(iPr$_3$Cp)$_2$.dme, Ba(tBu$_3$Cp)$_2$, Ba(tBu$_3$Cp)$_2$.thf, Ba(tBu$_3$Cp)$_2$.dme, Ba(thmd)$_2$, Ba(thmd)$_2$.triglyme, Ba(thmd)$_2$.tetraglyme, Ba(Me$_5$Cp)$_2$, Ba(Me$_4$Cp)$_2$, Ba(Me$_4$EtCp)$_2$, and Ba(Me$_4$nBuCp)$_2$.

11. A method of depositing a STO or BST film, the method comprising:
   providing an ALD reaction chamber having at least one substrate disposed therein;
   pulsing into the reaction chamber a precursor having the formula:

Ti(R$_1$—N═C(R$_3$)—N—R$_2$)$_u$(OR$_4$)$_x$(NR$_5$R$_6$)$_y$(O$_2$CR$_7$)$_z$    Formula I wherein:
   R$_1$, R$_2$, R$_5$, R$_6$, and R$_7$ are independently selected from the group consisting of H and C1-C6 alkyl group;
   R$_3$=H, C1-C6 alkyl group, or NMe$_2$;
   R$_4$ is a C1-C6 alkyl group;
   u=2;
   x=2;
   y=0; and
   z=0; and
   pulsing into the reaction chamber an oxygen source;
   pulsing into the reaction chamber a metal-containing precursor selected from the group consisting of M(L)$_2$ and M(L)$_2$.A, wherein:
   M is Sr or Ba;
   L is selected from substituted cyclopentadenyl ligand systems R$_1$R$_2$R$_3$R$_4$R$_5$Cp or beta-diketonate ligand systems —O—CR$_6$—CH—CR$_7$—O—;
   each of R$_1$ to R$_5$ is independently selected from H or C1-C6 linear or branched alkyl chain;
   each of R$_6$ and R$_7$ is independently selected from C1-C6 linear or branched alkyl chain; and
   A is a neutral oxygen containing molecules selected from the group consisting of tetrahydrofuran, dimethoxyethane, diglyme, triglyme, and tetraglyme;
   pulsing into the reaction chamber a second oxygen source; and
   controlling the stoichiometry of M:Ti ratio in the STO or BST film by varying a number of the pulsing steps for the precursor and metal-containing precursor.

12. The method of claim 11, wherein R$_1$ and R$_2$ are independently Et or iPr, R$_3$ is H or Me, and R$_4$ is a C1-C4 linear or branched alkyl chain.

13. The method of claim 11, wherein the precursor is selected from the group consisting of Ti(iPr—N═C(H)—N-iPr)$_2$(OiPr)$_2$, Ti(iPr—N═C(H)—N-iPr)$_2$(OMe)$_2$, Ti(iPr—N═C(H)—N-iPr)$_2$(OEt)$_2$, Ti(iPr—N═C(H)—N-iPr)$_2$(OnPr)$_2$, Ti(iPr—N═C(H)—N-iPr)$_2$(OsBu)$_2$, Ti(iPr—N═C(H)—N-iPr)$_2$(OiBu)$_2$, Ti(iPr—N═C(H)—N-iPr)$_2$(OtBu)$_2$, Ti(Et-N═C(H)—N-Et)$_2$(OiPr)$_2$, Ti(Et-N═C(H)—N-Et)$_2$(OMe)$_2$, Ti(Et-N═C(H)—N-Et)$_2$(OEt)$_2$, Ti(Et-N═C(H)—N-Et)$_2$(OnPr)$_2$, Ti(Et-N═C(H)—N-Et)$_2$(OsBu)$_2$, Ti(Et-N═C(H)—N-Et)$_2$(OiBu)$_2$, Ti(Et-N═C(H)—N-Et)$_2$(OtBu)$_2$, Ti(iPr—N═C(Me)-N-iPr)$_2$(OiPr)$_2$, Ti(iPr—N═C(Me)-N-iPr)$_2$(OMe)$_2$, Ti(iPr—N═C(Me)-N-iPr)$_2$(OEt)$_2$, Ti(iPr—N═C(Me)-N-iPr)$_2$(OnPr)$_2$, Ti(iPr—N═C(Me)-N-iPr)$_2$(OsBu)$_2$, Ti(iPr—N═C(Me)-N-iPr)$_2$(OiBu)$_2$, Ti(iPr—N═C(Me)-N-iPr)$_2$(OtBu)$_2$, Ti(Et-N═C(Me)-N-Et)$_2$(OiPr)$_2$, Ti(Et-N═C(Me)-N-Et)$_2$(OMe)$_2$, Ti(Et-N═C(Me)-N-Et)$_2$(OEt)$_2$, Ti(Et-N═C(Me)-N-Et)$_2$(OnPr)$_2$, Ti(Et-N═C(Me)-N-Et)$_2$(OsBu)$_2$, Ti(Et-N═C(Me)-N-Et)$_2$(OiBu)$_2$, and Ti(Et-N═C(Me)-N-Et)$_2$(OtBu)$_2$.

14. The method of claim 11, wherein the molecule is Ti(iPr—N═C(H)—N-iPr)$_2$(OiPr)$_2$ or Ti(iPr—N═C(Me)-N-iPr)$_2$(OiPr)$_2$.

15. The method of claim 11, wherein the metal-containing precursor is selected from the group consisting of Sr(iPr$_3$Cp)$_2$, Sr(iPr$_3$Cp)$_2$.thf, Sr(iPr$_3$Cp)$_2$.dme, Sr(tBu$_3$Cp)$_2$, Sr(tBu$_3$Cp)$_2$.thf, Sr(tBu$_3$Cp)$_2$.dme, Sr(thmd)$_2$, Sr(thmd)$_2$.triglyme, Sr(thmd)$_2$.tetraglyme, Sr(Me$_5$Cp)$_2$, Sr(Me$_4$Cp)$_2$, Sr(Me$_4$EtCp)$_2$, Sr(Me$_4$nBuCp)$_2$, Ba(iPr$_3$Cp)$_2$, Ba(iPr$_3$Cp)$_2$.thf, Ba(iPr$_3$Cp)$_2$.dme, Ba(tBu$_3$Cp)$_2$, Ba(tBu$_3$Cp)$_2$.thf, Ba(tBu$_3$Cp)$_2$.dme, Ba(thmd)$_2$, Ba(thmd)$_2$.triglyme, Ba(thmd)$_2$.tetraglyme, Ba(Me$_5$Cp)$_2$, Ba(Me$_4$Cp)$_2$, Ba(Me$_4$EtCp)$_2$, and Ba(Me$_4$nBuCp)$_2$.

16. The method of claim 11, wherein the oxygen source and the second oxygen source are water.

* * * * *